United States Patent
Moser et al.

(10) Patent No.: US 10,653,439 B2
(45) Date of Patent: May 19, 2020

(54) PUMP MODULE

(71) Applicant: Medaxis AG, Baar (CH)

(72) Inventors: Beat Moser, Uerzlikon (CH); Adrian Zweifel, Jona (CH); Beat Widmer, Lucerne (CH); Martin Butler, Hohenrain (CH); Lukas Christen, Lucerne (CH); Roman Good, Zürich (CH); Daniel Napoletano, Eglisau (CH)

(73) Assignee: Medaxis AG, Baar (CH)

( * ) Notice: Subject to any disclaimer, the term of this patent is extended or adjusted under 35 U.S.C. 154(b) by 275 days.

(21) Appl. No.: 15/621,505

(22) Filed: Jun. 13, 2017

(65) Prior Publication Data

US 2017/0354432 A1 Dec. 14, 2017

(30) Foreign Application Priority Data

Jun. 14, 2016 (EP) .................................... 16174475

(51) Int. Cl.
| | | |
|---|---|---|
| *F04B 53/14* | (2006.01) | |
| *A61B 17/3203* | (2006.01) | |
| *F04B 53/22* | (2006.01) | |
| *F04B 53/00* | (2006.01) | |
| *F04B 1/02* | (2006.01) | |
| *A61B 17/00* | (2006.01) | |
| *F04B 49/06* | (2006.01) | |

(52) U.S. Cl.
CPC ............ *A61B 17/3203* (2013.01); *F04B 1/02* (2013.01); *F04B 53/008* (2013.01); *F04B 53/143* (2013.01); *F04B 53/22* (2013.01); *A61B 2017/00477* (2013.01); *F04B 49/06* (2013.01); *F04B 2201/124* (2013.01)

(58) Field of Classification Search
CPC ... A61B 17/3203; F04B 53/143; F04B 53/147
See application file for complete search history.

(56) References Cited

U.S. PATENT DOCUMENTS

| | | |
|---|---|---|
| 3,922,115 A | 11/1975 | Coe et al. |
| 5,667,141 A | 9/1997 | Suttner |
| 6,032,349 A | 3/2000 | Wagner et al. |
| 7,553,318 B2 | 6/2009 | Ammann |
| 8,177,524 B1 | 5/2012 | Kieffer et al. |

(Continued)

FOREIGN PATENT DOCUMENTS

| | | |
|---|---|---|
| CN | 101677825 A | 3/2010 |
| CN | 103470466 A | 12/2013 |

(Continued)

OTHER PUBLICATIONS

European Search Report, Application No. 16174475.0, dated Nov. 25, 2016.

*Primary Examiner* — Patrick Hamo
(74) *Attorney, Agent, or Firm* — Fishman Stewart PLLC

(57) ABSTRACT

A pump module with a casing having at least one pump piston is mounted in a reciprocatingly movable manner and may include a sealing element which, in pumping operation, abuts in a sealing manner against a cylinder. An embodiment of a pump module, which is easy to produce and can be disinfected or sterilized in a simple manner, includes a pump piston that can be fixated in a parking position in which the sealing element does not abut against the cylinder.

14 Claims, 15 Drawing Sheets

(56) References Cited

U.S. PATENT DOCUMENTS

| | | | |
|---|---|---|---|
| 8,328,831 B2 * | 12/2012 | Pein | A61B 17/3203 417/536 |
| 8,826,646 B2 * | 9/2014 | Waletzek | F04B 35/045 60/286 |
| 8,851,866 B2 * | 10/2014 | Moutafis | A61B 17/3203 417/214 |
| 9,057,363 B2 | 6/2015 | Capone et al. | |
| 9,938,971 B2 * | 4/2018 | Moser | A61B 17/3203 |
| D832,999 S * | 11/2018 | Moser | A61B 17/3203 D24/111 |
| 2001/0002562 A1 | 6/2001 | Moutafis et al. | |
| 2002/0176788 A1 * | 11/2002 | Moutafis | A61B 17/3203 417/415 |
| 2007/0286754 A1 | 12/2007 | Laing | |
| 2008/0202507 A1 | 8/2008 | Brandli | |
| 2008/0221602 A1 | 9/2008 | Kuehner et al. | |
| 2009/0242470 A1 | 10/2009 | Muenkel et al. | |
| 2010/0049228 A1 | 2/2010 | Kuehner et al. | |
| 2011/0150680 A1 | 6/2011 | Dion et al. | |
| 2012/0051956 A1 | 3/2012 | Grip | |
| 2012/0152248 A1 * | 6/2012 | Richey, II | B01D 53/04 128/204.18 |
| 2012/0224987 A1 * | 9/2012 | Jones | F04B 17/04 417/420 |
| 2014/0079580 A1 | 3/2014 | Habe | |
| 2014/0093406 A1 | 4/2014 | Dorfler et al. | |

FOREIGN PATENT DOCUMENTS

| | | |
|---|---|---|
| DE | 29611935 U1 | 9/1996 |
| DE | 10160168 A1 | 6/2003 |
| DE | 102004031673 A1 | 1/2006 |
| DE | 102006053609 A1 | 5/2008 |
| DE | 102014016141 A1 | 5/2016 |
| EP | 1296601 B1 | 8/2006 |
| EP | 1924305 B1 | 2/2010 |
| WO | WO-0197700 A2 | 12/2001 |
| WO | WO-2007031304 A1 | 3/2007 |
| WO | WO-2008086950 A1 | 7/2008 |

* cited by examiner

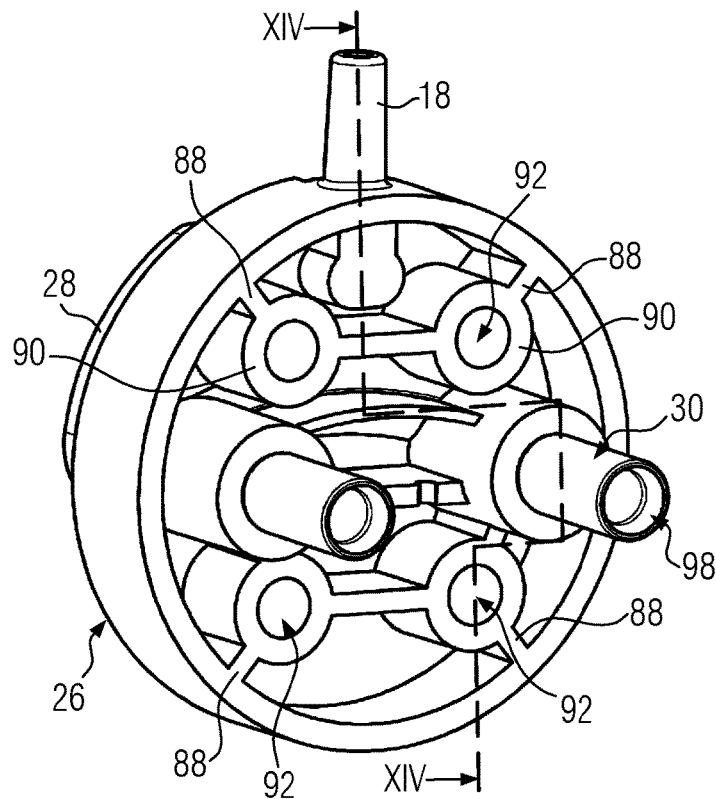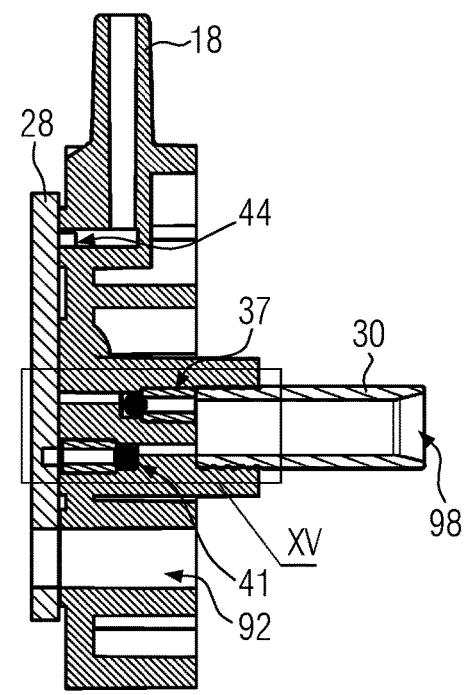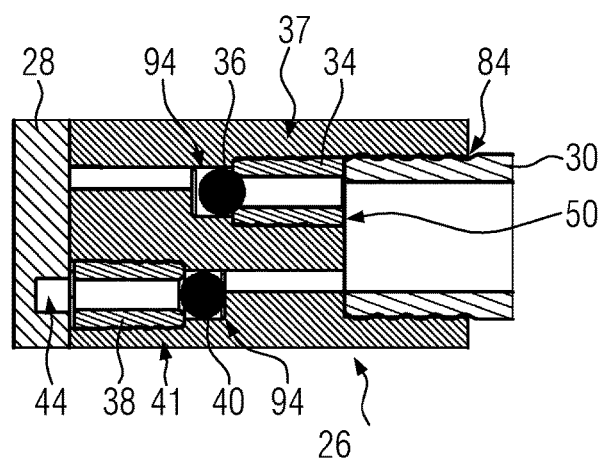
FIG. 13
FIG. 14
FIG. 15

PUMP MODULE

CROSS-REFERENCE TO RELATED APPLICATIONS

This application claims priority to European Patent Application No. 16174475.0, filed Jun. 14, 2016, the contents of which are hereby incorporated by reference in its entirety.

TECHNICAL FIELD

The present invention relates to a pump module. The present invention in particular intends to specify a pump module which can be produced inexpensively.

BACKGROUND

The present invention in particular intends to provide a pump module for medical purposes, especially for the valve and by way of a water jet. In this procedure, a concentrated water jet is jetted onto a wound in order to remove scab to promote healing of the wound.

Since it must with this procedure be avoided that germs and contaminants are in the course of the treatment again introduced into the wound, the respective pump module must be sterilizable or already be entered into the market and packaged in a sterilized manner before the pump module is used in the framework of the therapy. This, in turn, requires the production of the pump module in sterile conditions, which is costly.

It is likewise costly to dismantle the pump module into its essential components and to sterilize it prior to its use. This is because the pump module according to the invention is commonly a disposable article which is usually used only once.

SUMMARY

The present invention relates in particular to a pump module with a casing in which at least one pump piston is mounted in a reciprocatingly movable manner and is provided with at least one sealing element which in pumping operation abuts in a sealing manner against a cylinder. Such a pump module for use in surgery is known, for example, from US 2010/0049228. This pump module has a bellows for each pump piston extending between the casing and the pump piston in order to seal the region interacting with the cylinder against the environment and thereby prevent the ingress of bacteria.

Such pump modules of the type mentioned above are known, for example, from US 2002/0176788 A1, US 2014/0079580 A1, or US 2011/0150680 A1. Sometimes these previously known pump modules are referred to as sterilizable.

There are various ways to sterilize or disinfect medical equipment. However, contact between the disinfecting or sterilizing agent and the parts to be sterilized is necessary for effective preparation of surgical equipment. In the pump modules of the type mentioned above, the sealing element during the pumping operation abuts the pump piston in a sealing manner which makes it difficult or impossible to obtain effective sterilization or disinfection in this region. But the fluid to be jetted onto the body is pumped precisely there. For effective preparation of the pump module, the necessity therefore exists to remove the pump piston from the casing, to sterilize it and to assemble the components after sterilization.

The present invention intends to provide a pump module of the type mentioned above which can be produced inexpensively and can be easily sterilized or disinfected.

In order to satisfy this object, it is with the present invention proposed that the pump piston can be fixated in a parking position. In this parking position, the sealing element does not abut against the cylinder. A cylinder is within the meaning of the present invention considered to be the region against which the sealing element abuts in a sealing manner. The cylinder may be formed by the material forming the housing or a part thereof and may be integral with the housing or a part thereof. The sealing element is therefore in contact with the cylindrical inner circumferential surface of the cylinder. In the parking position, the sealing element is located outside this region of the cylinder with a cylindrical inner circumferential surface.

The pump module according to the invention commonly has a drive region to which the cylinder is open, and at which the pump piston with its end on the drive side is exposed in order to be connected to a drive. The rack receiving the drive usually has a seat for the pump module so that the latter can be fixated and fixedly connected to the drive. Disposed on the opposite side of the drive region is a discharge area in which a discharge opening for the pressurized fluid is located. On the basis of this structural design, the sealing element is in the parking position commonly disposed ahead of the cylinder, i.e., ahead of in the direction of the drive region, so that the pump piston must for the pump operation first be advanced from the parking position in the direction towards the discharge region in order to abut the sealing element in a sealing manner against the cylinder. This motion commonly corresponds to the joining motion of the pump module for coupling the pump piston to the drive so that the pump piston is in the embodiment presently discussed in a simple manner moved from the parking position to a pumping position in pumping operation so that the pump module after being coupled to the drive necessarily has a pump piston provided in the pumping operation. Switching on the drive therefore immediately allows operation of the pump module for discharging a fluid jet.

In the pump module according to the invention, fixating the pump piston in the parking position is realized. Any device is conceivable as a fixation device which provides a certain resistance to a displacement motion of the pump piston relative to the casing, but when the predetermined axial force is exceeded does not prevent the pump piston from being axially displaced into an operating position in which the sealing element abuts the inner circumferential surface of the cylinder in a sealing manner so that the reciprocating operation of the pump piston pressurizes and discharges fluid within the pump module. An external or separate locking element can be provided as a fixation device which fixates the pump piston relative to the casing and which must prior to operation be removed in order to make the pump piston be reciprocatingly movable within the casing. Such a fixation device can be, for example, a retaining ring which circumferentially surrounds the pump piston externally, is connected in a positive-fit manner thereto, and interacts with or abuts against a counter-surface being formed by the casing to prevent advancement of the pump piston to one of the pump positions and to fixate the parking position.

Though such embodiments are indeed conceivable, they have the disadvantage that disengaging the parking position is complex. According to a preferred development of the present invention, a locking element is proposed which in the parking position interacts with a locking counter-element provided on the pump piston, where the locking element is preferably arranged on the casing and connected thereto. The locking element is preferably integrally formed on the casing. It is conceivable to produce the casing and therefore also the locking element from plastic material. The locking element can be, for example, an engaging pawl which is formed integrally on the casing and is elastically preloaded radially against the pump piston in order to interact with the latter in the parking position and to fixate it in the parking position. The locking device can there interact in a frictionally engaged and/or in a positive-fit manner with the pump piston.

According to a preferred embodiment of the present invention, however, a positive-fit connection is proposed in which the locking element or the locking counter-element comprises two radial projections provided at an axial distance from one another between which the other of the locking element or the locking counter-element engages in the parking position. A groove is accordingly formed by the radial projections and is suitable for engagement in a positive-fit manner. The radial projections can there be formed by shaping a groove on a cylindrical outer circumferential surface of the pump piston. In this case, the radial projections elevate only radially outwardly<from the base of the groove to the smooth outer circumferential surface of the piston. However, the radial projections can equally well project radially outwardly over the substantially cylindrical pump piston, whereby defined guide surfaces can be formed that can in pumping operation be guided on a cylinder wall of the casing which is disposed axially ahead of the cylinder. This cylinder wall is commonly formed by a guide cylinder that is formed by the casing. This prevents the pump piston from buckling during operation. Good axial alignment of the pump piston is also made possible by guidance, firstly, via the sealing element and, secondly, via the locking counter-element.

According to a preferred development of the present invention, a conical feed-in device is provided disposed ahead of the cylinder. This conical feed-in device is preferably provided directly ahead of the cylinder. The feed-in device has a small inner diameter which substantially corresponds to the inner diameter of the cylinder. Assembly of the pump piston together with the sealing element can be simplified by way of this conical feed-in device. The conical feed-in device is in particular configured such that it takes the sealing element substantially to an outer diameter that corresponds to the inner diameter of the cylinder, whereby the sealing element is arranged concentrically relative to the cylinder so that the introduction of the sealing element into the cylinder is facilitated. The conical feed-in device can there be provided on the casing.

In view of the most effective use of the reciprocating motion of the drive for pumping, it is according to a preferred embodiment of the present invention proposed to provide the sealing element in the conical feed-in device in the parking position. Slight axial displacement of the pump piston after joining the pump module to the drive accordingly directly leads to the sealing element being located within the cylinder and therefore in a pumping position. This is in particular the case where the conical feed-in device is formed at the entrance of the cylinder and transitions in a flush manner to the cylinder surface.

According to a preferred development of the present invention, the conical feed-in device can be formed by a cylinder insert against which the sealing element during the pumping operation sealingly abuts. This embodiment offers the advantage that the casing can be produced predominantly from low-cost plastic material, the sealing surface of the cylinder interacting with the sealing element in which a cylinder insert made, for example, from technically high-grade plastic material or from metal can be inserted into the casing in a sealing manner [sic]. Possible suitable plastic materials for producing the pump module or parts thereof are PA, PE, PP and/or POM. The development is therefore suitable for an inexpensive production of the pump module at good precision and alignment between the sealing element and the insulating jacket surface of the cylinder, which should with its diameter preferably be exactly matched to the outer diameter of the sealing element and should have a good surface quality and a smooth design.

According to a further preferred embodiment of the present invention, the pump piston comprises a plunger body which at one end comprises a positive-fit element for coupling the piston to the drive associated with the piston and at its other end is provided with a seat for the sealing element. This plunger body there preferably forms the entire pump piston, where the plunger body usually forms attachment devices, such as, for example, positive-fit devices which hold the sealing element on the plunger body. The plunger body can there be made of plastic material and therefore be produced inexpensively.

In the development previously discussed, the positive-fit element in the parking position preferably projects over the casing so that an optical indicator is given for the user of the pump for determining whether the pump piston had been located in the parking position before and after the disinfection or sterilization. The pump piston can likewise be provided with a different optical indicator, for example, have a color or contoured design, the position of which can be verified, for example, by a viewing window formed on the casing in order to verify whether the pump piston is actually located in the parking position and that preparation of the pump module has occurred in a sufficient manner complying with the requirements prior to use by disinfection or sterilization. The disinfection can be performed, for example, by introducing ethylene oxide gas into the pump module (ethylene oxide (EO) sterilization). This gas also flows around the pump piston being disposed in the parking position and also the sealing element, so that the latter is completely comprised by the disinfection.

The gap provided in the parking position between the outer circumference of the sealing element and the inner circumference of the walls of the casing surrounding the sealing element is at least $1/10$ mm, preferably at least $2/10$ mm, and particularly preferably at least $3/10$ mm. With regard to a rapid transition of the pump piston from the parking position to an operating or pumping position in which the sealing element sealingly abuts against the cylinder, the sealing element is in the parking position preferably disposed close to the cylinder. The abovementioned gap can there be formed by the conical feed-in device or other region which is commonly formed by the casing and which is preferably disposed directly ahead of the cylinder. When setting the gap dimension, free passage of the disinfecting agent is essential so that it can coat all surfaces of the sealing element.

Sealing element is in the present invention understood to mean any element which is capable of sealingly abutting against the inner circumferential wall of the cylinder in order to enable a pumping operation. The sealing element can there also be integrally formed on the pump piston.

According to a preferred embodiment of the present invention, the one end is in the parking position protruded by the casing and/or is covered by a cover cap detachably connected to the casing. This development is intended to prevent the pump piston from being displaced prior to installation to a drive direction and prior to disinfection inadvertently from the parking position to an operating position in which the sealing element sealingly abuts the cylinder.

The casing preferably has a shape configuration which makes it possible to join the casing to the drive in a motion substantially corresponding to the axial motion of the reciprocatingly movable pump piston. For this purpose, the casing commonly has guide surfaces extending parallel to the direction of motion of the pump piston and allowing the pump module to be inserted into a frame or casing of the drive in order to abut the pump piston with its end on the drive side against the drive and thereby, within the framework of joining the pump module and the drive, to preferably couple the pump piston to the drive in such a manner that the pump piston is during operation of the drive moved in a reciprocating manner. In this joining motion, the piston is preferably moved from the parking position to a pumping position. Within the framework of the installation of the pump module into the casing or the frame of the drive, respectively, a positive-fit connection is preferably effected between the positive-fit element of the pump piston and the drive within the framework of the installation of the pump module into the casing or the frame of the drive, respectively.

BRIEF DESCRIPTION OF THE DRAWINGS

Further details and advantages of the present invention shall become apparent from the following description of an embodiment in combination with the drawing, in which:

FIG. 13 shows a perspective rear view of the pump unit according to FIG. 2;

FIG. 14 shows a sectional view along line XIV-XIV, according to the view in FIG. 13;

FIG. 15 shows detail XV according to FIG. 14;

DETAILED DESCRIPTION

Figure 1:
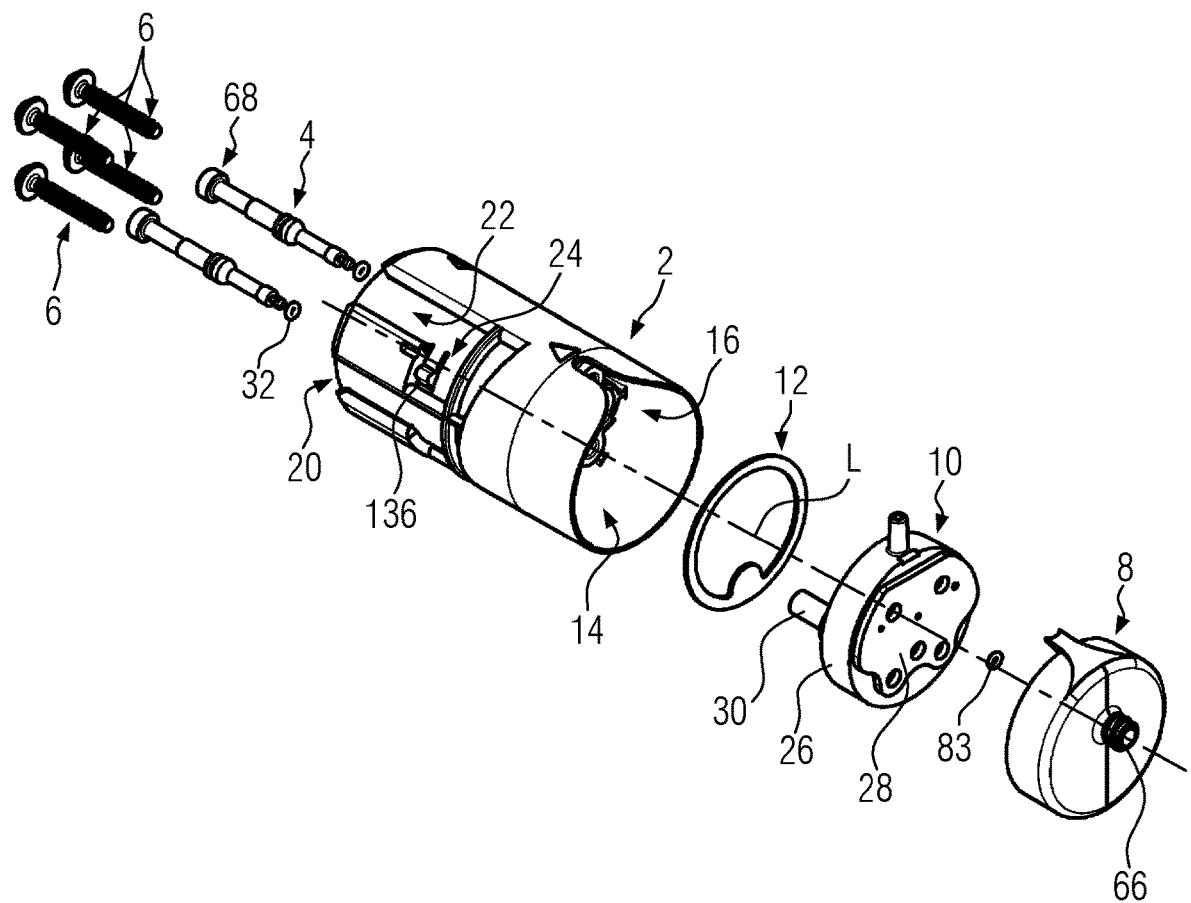
FIG. 1 shows a first exploded view of the embodiment.

FIG. 1 shows the essential components of the embodiment according to the present invention, which is a pump module. The pump module comprises a casing base 2 which accommodates two plunger bodies 4 within itself and surrounds them in a reciprocatingly movable manner. Furthermore, four tensioning screws 6 are shown which are embodiments of tensioning elements within the meaning of the present invention and in the assembled state engage with a head element 8 that is disposed ahead of a pump unit 10 being received in casing base 2 while an annular RFID element 12 is interposited, which is an example of a transponder unit of the present invention. The casing base 2 for this purpose has a discharge region 14 which is configured as a cylindrical seat on the casing base 2, where an axial slot 16 is formed adapted to receive an inlet port 18 of the pump unit 10. The casing base 2 is likewise open at the end opposite to the discharge region 14 and forms a drive region 20.

Figure 18:
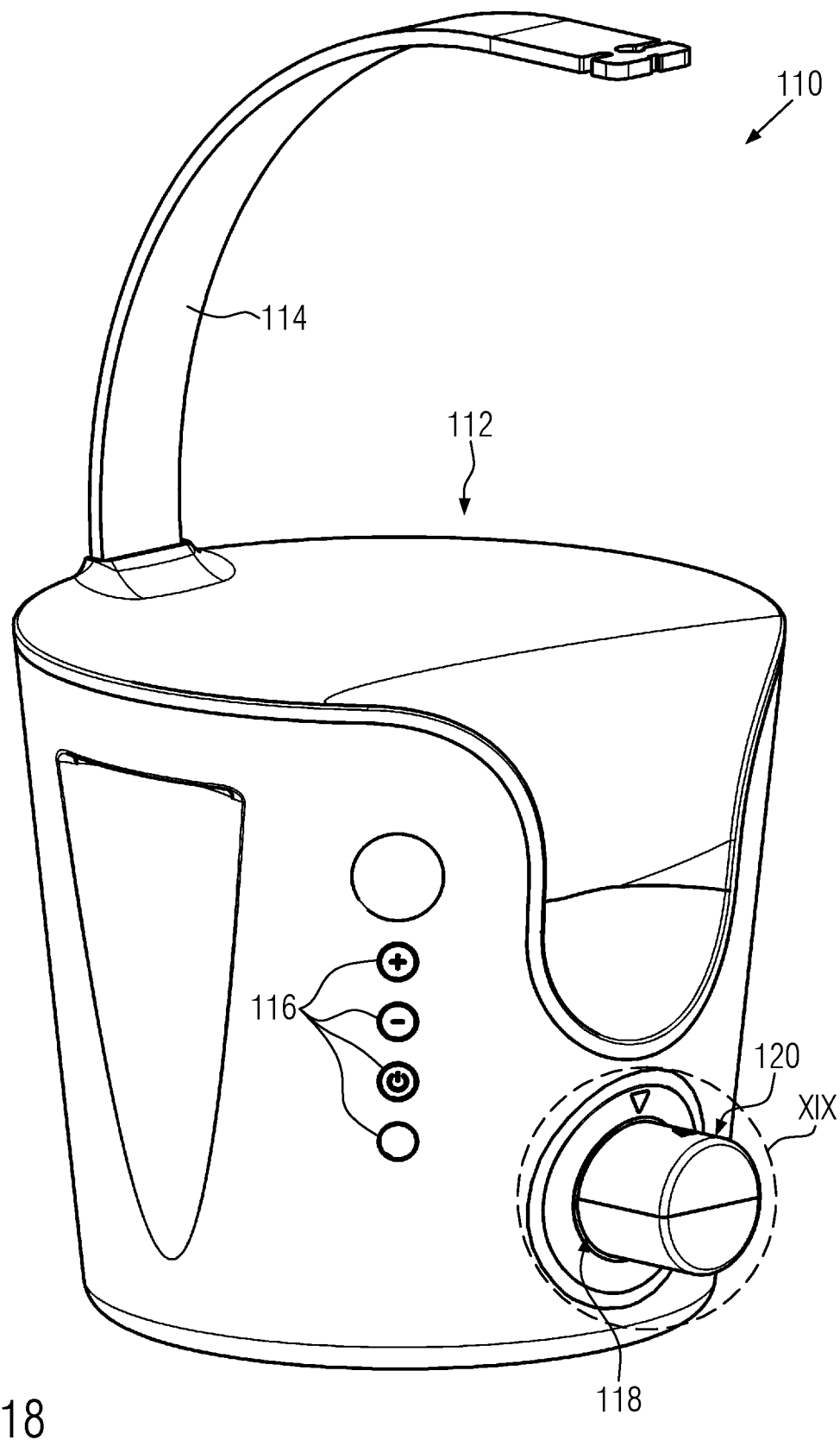
FIG. 18 shows a perspective view of an embodiment of a device for producing a fluid jet.

As can be seen in FIG. 1, the casing base is formed to be substantially cylindrical. Formed on the outer circumferential surface on the casing base 2 are grooves 22 extending in the axial direction of the casing base 2 and transverse grooves 24 branching therefrom and extending transversely thereto which represent the guide and locking surfaces for attaching the pump module to a drive casing, the details of which are illustrated in FIG. 18 et seqq. and the associated description.

The pump unit 10 is formed by a valve block 26 and a cover element 28 abutting thereagainst, where two cylinder inserts 30 project from the valve block 26 on the side disposed opposite to the cover element 28, of which only one cylinder insert 30 can be seen in FIG. 1 and which during the pumping operation interact with the plunger bodies 4. For this purpose, the plunger bodies 4 each carry a sealing element 32 in the form of a sealing ring which is in the region of the front free end of the plunger body 4 held thereon in a positive-fit manner.

Figure 2:
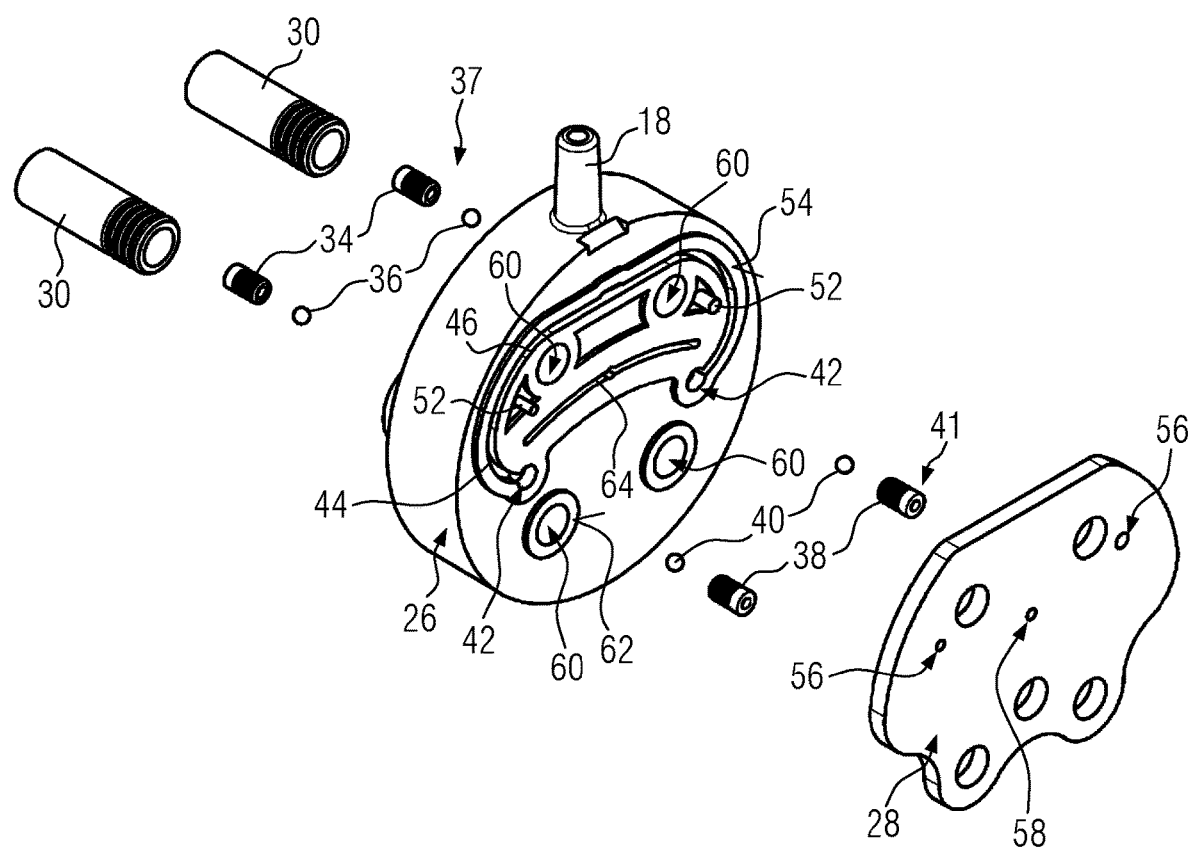
FIG. 2 shows an exploded view according to FIG. 1 for a pump unit of the embodiment shown in FIG. 1.

FIG. 2 shows that the two cylinder inserts 30 on their end facing the valve block 26 comprise a wavelike contour on their outer circumference which are formed into the valve block 26 for the sealing insertion of the cylinder inserts 30. A respective valve liner 34 is provided between the cylinder inserts 30 and the valve block 26 and together with a valve ball 36 each forms an outlet valve 37. Valve liners 38 with associated valve balls 40 are illustrated on the side opposite to the cylinder inserts 30 and form inlet valves 41 to the respective cylinder inserts 30. The inlet valves 41 are received in inlet valve bores 42 which are recessed in the valve block 26 and communicate with an inlet passage 44 which is recessed in a projection 46 as a U-shaped groove being open on one side and which is covered by the cover element 28. The outlet valves 37 are seated in corresponding outlet valve bores, one of which is shown by way of example in FIG. 9 and is provided with reference numeral 50. As illustrated in FIG. 2, inlet port 18 is integrally formed on the valve block 26. From the side facing the cover element 28, two fitting elements 52 of different diameters protrude from and project beyond the sealing surface 54 formed by the projection 46. The cover element 28 has bores 56 formed adapted for these fitting elements 52 which serve to correctly position the cover element 28 relative to the valve block 26. The fitting elements 52 and the fitting bores 56 there have mutually adapted diameters so that the cover element 28 is according to a poka-yoke function always arranged in the correct orientation and position when assembling the cylinder insert 30 on the valve block 26.

In addition to these two fitting bores 56, the cover element 28 also comprises an outlet bore 58.

The valve block 26 comprises four through bores 60 corresponding to the tensioning screws 6 and which, firstly, pass through the sealing surface 54 formed by the projection 46 and, secondly, annular surfaces 62 which are configured to be adapted for the abutment against the cover element 28 and are provided at the same height. The cover element 28 abuts sealingly against the surfaces 62 and 54 and is welded thereon by laser beam welding. For this purpose, the cover element 28 is formed from laser-transparent material, whereas the valve block 46 is formed from plastic material absorbing laser beams. Both parts can accordingly be connected by way of laser transmission welding, where the cover element 28 made of plastic material is at the phase boundary to the valve block connected in a positive substance-fit manner to the plastic material of the valve block 26. The inlet passages 44 and an the outlet passages, designated by reference numeral 64 and comprising a U-shaped channel recessed on the valve block 26 and covering the cover element 28, are formed thereby. The outlet passage 64 is via the outlet bore 58 in communication with an outlet port bushing 66 being integrally formed on the head element 8 and being provided in axial extension of the outlet bore 58 and provided with an external thread on its outer circumference for forming a Luer connection. A pressure hose can accordingly by way of a Luer connection be connected in a simple way to the outlet port bushing 66.

Figure 4:
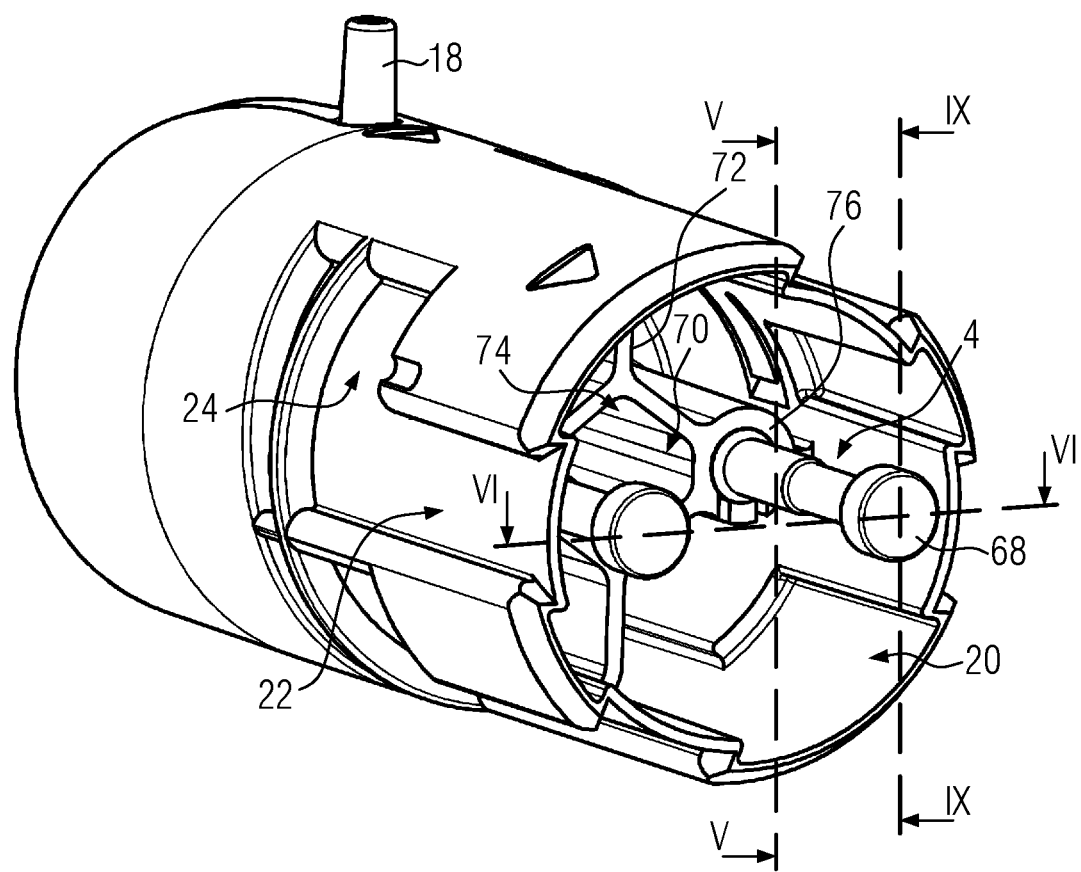
FIG. 4 shows a perspective side view according to FIG. 3 into the open drive region.

FIG. 4 shows a perspective side view with a top view upon the face side end of the casing base 2 and of the drive region 20. The plunger bodies 4 are surrounded by the casing base 2 and with their one end project into the drive region 20. As is in particular evidenced by FIG. 5, the end of the plunger body 4 on the drive side, which forms a positive-fit element shaped as a hammer head 68, projects beyond the casing base 2 at the end side. Otherwise, however, the plunger body 4 is axially covered by the casing base (see FIG. 5).

As can be seen from a synopsis of FIGS. 4, 5, 6 and 11, the casing base 2 is configured as an injection-molded member with relatively uniform wall thicknesses, so that good solidification behavior is obtained during the injection-molding process of the casing base 2. Plastic materials for the production of the components of the module can be PA, PE, PP and/or POM, possibly as filled plastics, for example, filled with minerals and/or fibers. For this purpose, the casing base 2 has a center recess 70 which is via radial webs 72 connected to the outer circumferential surface of the casing base 2, where the radial webs 72 branch off from a polygon structure 74 which connects guide sleeves 76 between the radial webs 72 inwardly to the respective plunger bodies 4 which are supported via further radial webs 78 on the outer circumferential surface of the casing base 2 (cf. FIG. 16).

Figure 17:
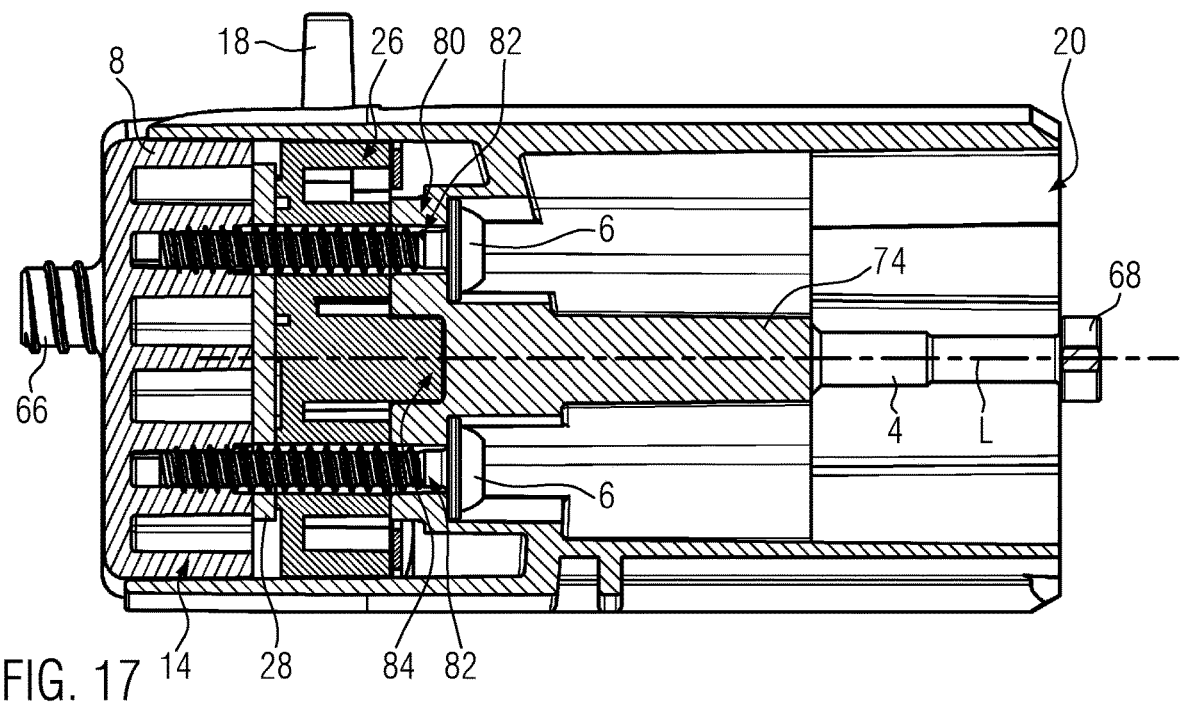
FIG. 17 shows a sectional view taken along line XVII-XVII according to FIG. 16, where the sectional plane includes the center longitudinal axes of the two tensioning screws 6 and extends parallel to the plane of motion of the pump piston.

The casing base 2 forms a radially extending partition wall 80 which is inter alia provided with passage bores 82 for the tensioning screws 6 (cf. FIG. 17). The tensioning screws 6 there completely penetrate the partition wall 80, the valve block 26 and the cover element 28, and partially the head element 8 and are in threaded engagement with the latter. For this purpose, the tensioning screws 6 are self-tapping. The head element 8 can also by welding be welded to the recess formed by the casing base 2 in the discharge region 14 and thereby be indirectly connected to the valve block 26 and the cover element 28. A sealing ring 83 seals the passage formed by the outlet port bushing 66 against the outlet bore 58 of the cover element 28 (cf. FIGS. 1 and 5).

Figure 8:
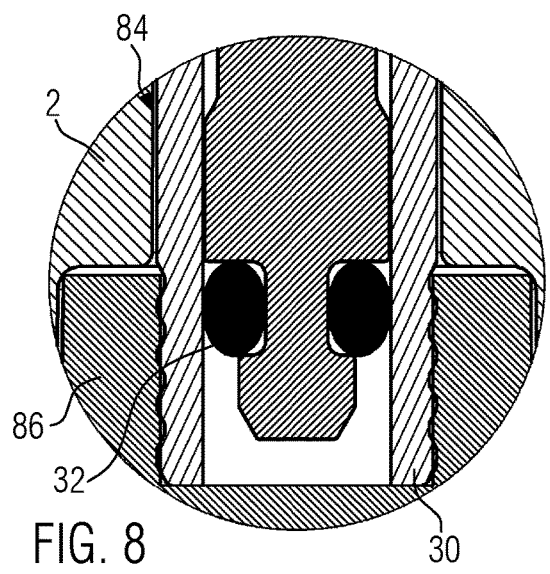
FIG. 8 shows enlarged detail VIII according to FIG. 6 for a pump piston penetrating deeper into the cylinder than in FIG. 6.

In the axial extension of the guide sleeves 76, the casing base 2 forms cylinder insert receiving bores 84 reaching up to the partition wall 80 which are formed adapted to receive the cylinder inserts 30 and which are radially thickened approximately at the height of the partition wall 80 in order to form between the cylinder insert 30 and the material of the casing base 2 an annular space into which a protruding ring collar 86 of the valve block 26 fits. This ring collar 86 is shown, for example, in FIGS. 6 and 9. The ring collar 86 serves to establish the sealing connection between the cylinder insert 30 and the valve block 26. As illustrated in FIG. 8, a contoured outer circumferential surface of the cylinder inserts 30 is there accommodated within the ring collar 86 and is also positively locked therewith Each cylinder insert 30 is by pressing inserted into the ring collar 86 and is thereby sealingly connected to the valve block 26.

Figure 5:
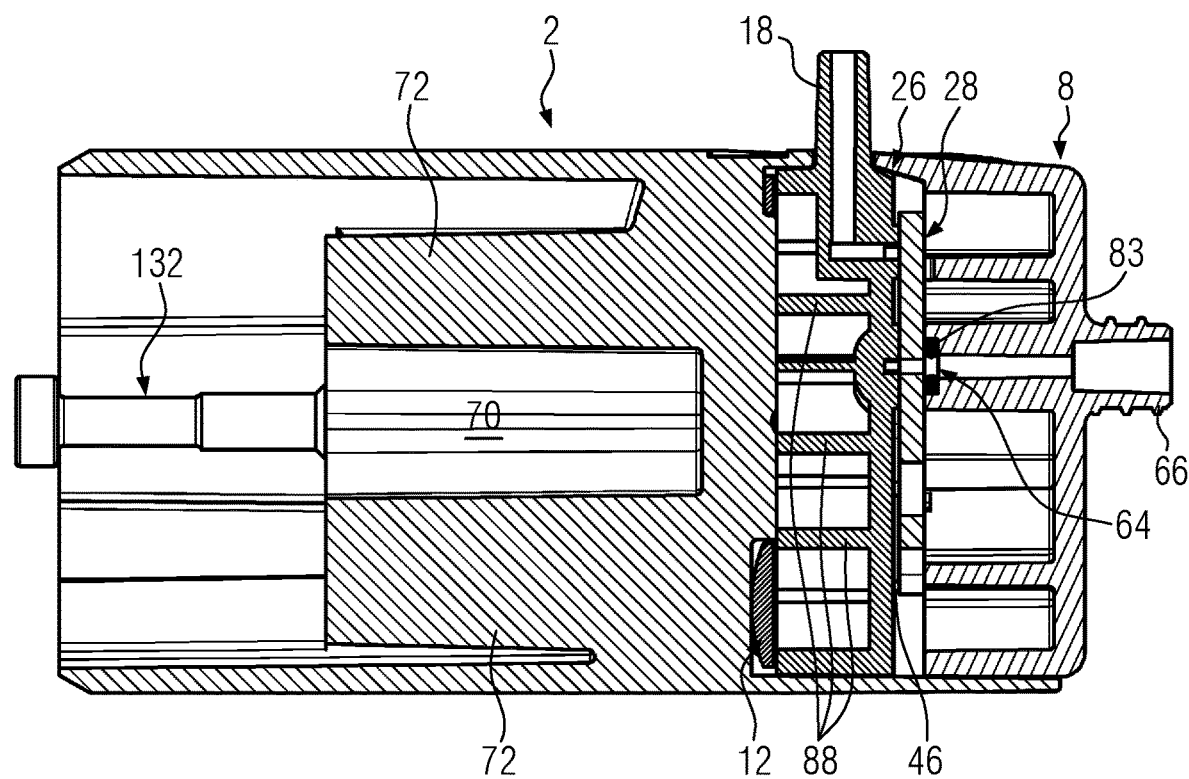
FIG. 5 shows a sectional view along the line V-V according to FIG. 4 and FIG. 11, respectively, where the sectional plane includes the center longitudinal axis of the pump module.

The partition wall 80 further forms an annular groove which opens toward the valve block 26 and is formed adapted to receive the RFID ring 12 so that this RFID ring 12 can be arranged between the partition wall 80 and the valve block 26 (cf. FIG. 5) FIG. 5 there in the lower part of this annular groove shows a thickening of the RFID ring 12 which represents the data carrier. The remainder of the region of the RFID ring 12 being slimmer in the radial direction serves for adequate positioning within the casing base 2 (cf. FIG. 1) and also as a coil for signal amplification of a signal outputted, for example, from a handpiece, with which the type of nozzle geometry installed in the handpiece is indicated.

As illustrated in FIGS. 5 and 13, the valve block 26 is also configured as a component having the same wall thicknesses and can therefore be produced well by way of plastic injection molding. in particular FIG. 5 illustrates several of support ribs 88 extending in the direction of motion of the plunger bodies 4 and being supported on the partition wall 80 and connecting sleeve segments 90 which form passage bores 92 for the tensioning screws 6 that are flush with the passage bores 82 through the partition wall 80, where the above-mentioned sleeve segments 90 form the previously mentioned annular surfaces 62 for abutment of the cover element 28.

FIGS. 14 and 15 illustrate the arrangements of the inlet and outlet valves 37, 41 in the valve block 26. This valve block 26 has bores 42, 50 being adapted to receive the corresponding valve lines 34 and 38, and each of which having a receiving space 94 downstream in the flow direction of the fluid in which the valve ball 36 or 40 are respectively located. In the closed state of the valve, this valve ball 36 or 40, respectively, interacts with a valve opening which is formed by the flow-free end of the corresponding valve liner 34, 38. This position is in FIG. 15 shown for the valve ball 36 of the outlet valve 37, whereas the valve ball 40 of the inlet valve 41 unblocks the corresponding valve opening. FIG. 15 shows a state in which the plunger body 4 increases the displacement within the cylinder insert 30 and the fluid to be pumped is introduced into the displacement chamber through the inlet passage 44, whereas the outlet passage is closed by the outlet valve 37. The respective valve balls 36, 40 are in the embodiment shown provided freely movably in the receiving space 34 and are captively held in the valve block 26 due to the diameter ratios between the valve opening and the diameter on the flow-remote side of the passage which branches from the valve opening and is formed in the valve block 26. For assembly, the respective ball 36, 40 is first inserted into the receiving space 94. The valve liner 34 or 38, respectively, is then pressed into the valve block 26. The valves 37, 41 are then preassembled in the valve block 26 in a captive manner.

As can further be seen in FIG. 15, the cylinder insert 30 pressed into the valve block 26 on the face side abuts against the valve liner 34 of the outlet valve 37, whereby the valve 37 provided on the pressure side of the pump is additionally secured in position and prevented from being undesirably pressed out from the force fit to the valve liner 36.

Figure 6:
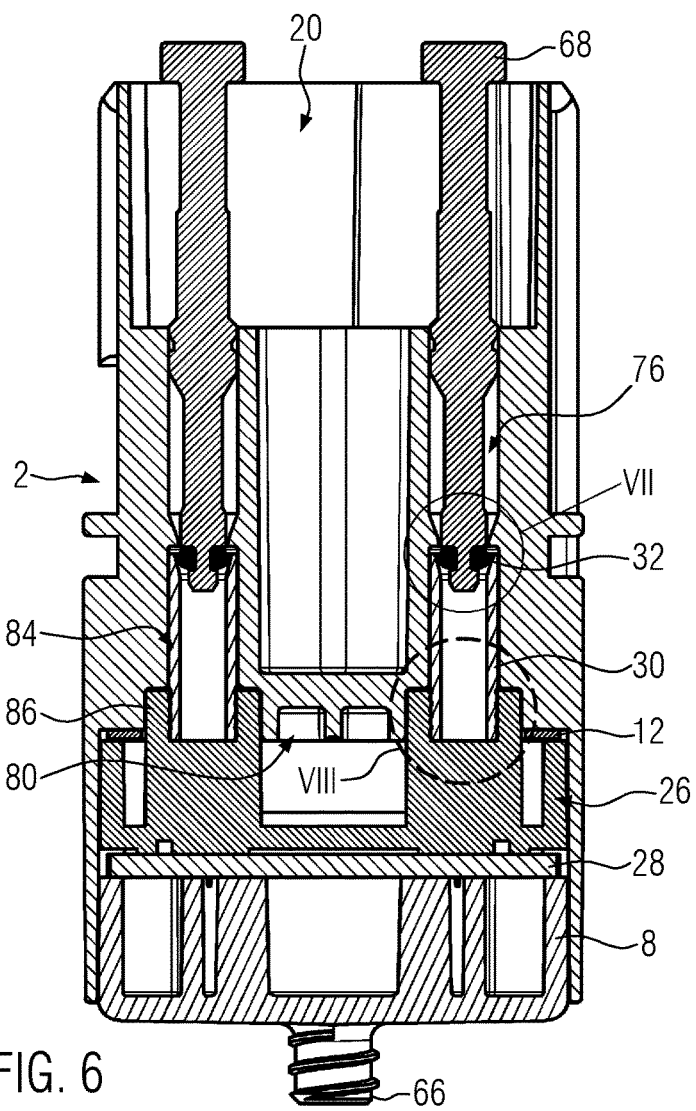
FIG. 6 shows a sectional view of FIG. 2 along the line V-V according to FIG. 4, where the sectional line includes the plane of motion of the pump piston.
Figure 7:
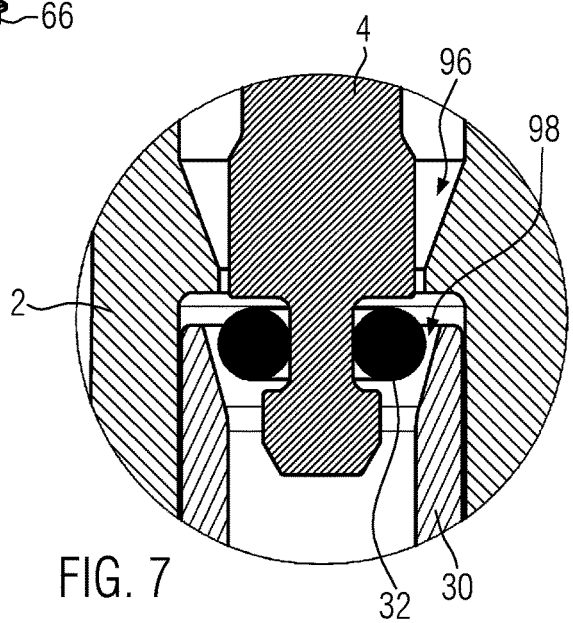
FIG. 7 shows enlarged detail VII according to FIG. 6.
Figure 9:
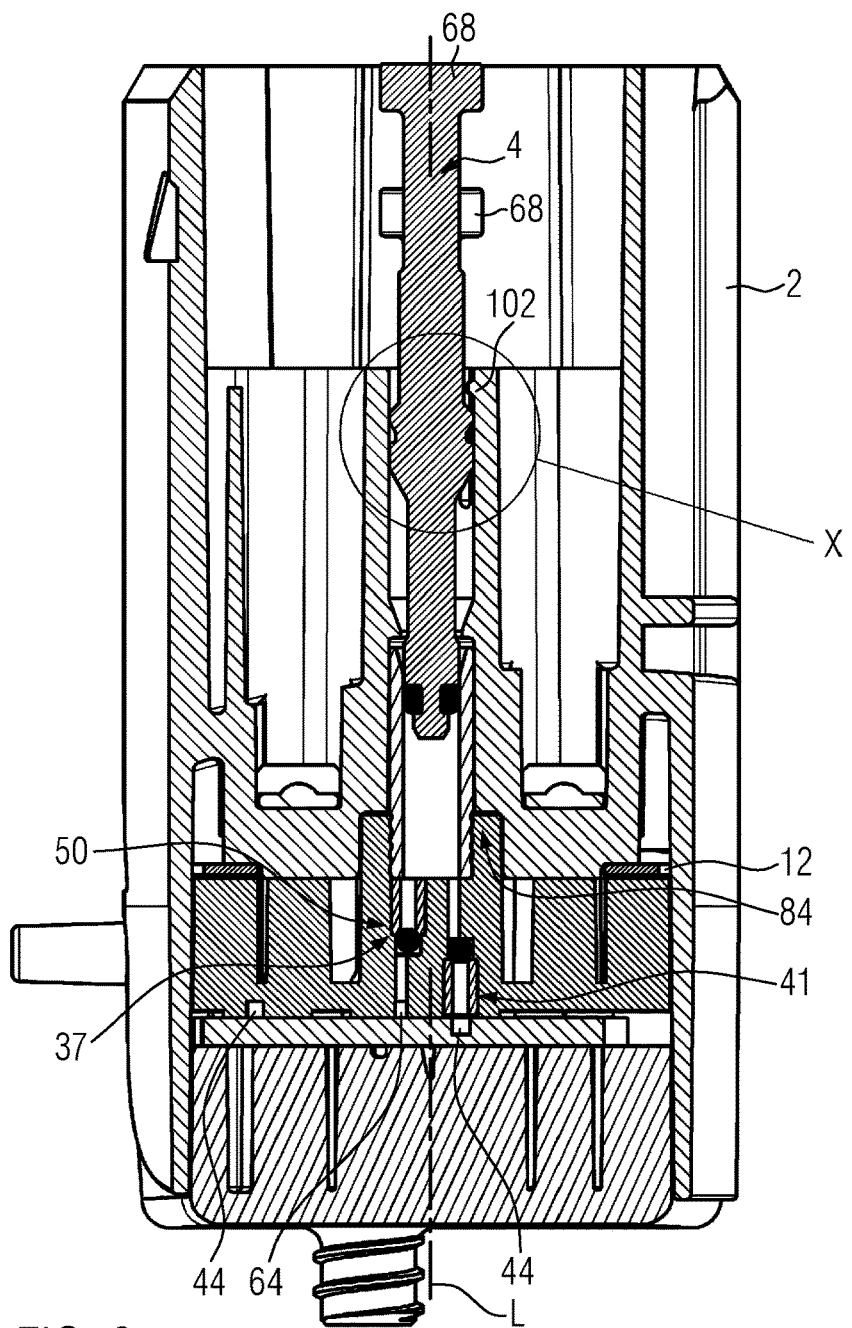
FIG. 9 shows a sectional view along line IX-IX according to FIG. 4, where the sectional plane includes the plane of motion and the center longitudinal axis of one of the pump pistons.
Figure 10:
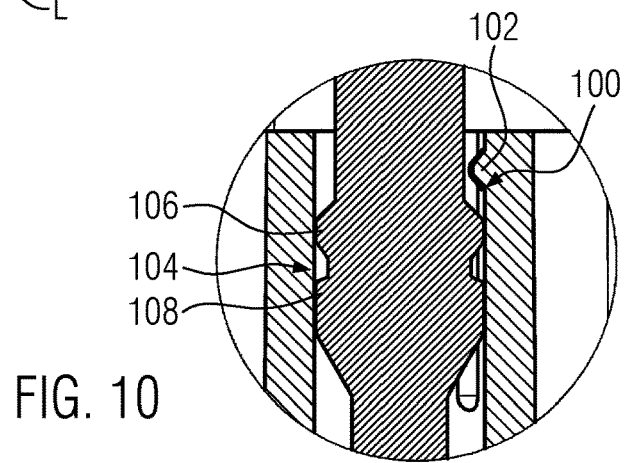
FIG. 10 shows enlarged detail X according to FIG. 9.

In particular FIG. 7 illustrates a first conical feed-in device 96 which is formed by the casing base 2 and which is provided ahead of the cylinder insert 30 in the direction of the drive region 20. This first conical feed-in device 96 facilitates the insertion of the plunger body 4 with its front end, on which the sealing element 32 is located, into the cylinder formed by the cylinder insert 30. When the plunger body 4 is inserted, the sealing element 32 is arranged concentrically with respect to the cylinder insert 30 and brought approximately to the latter's inner diameter. A second conical feed-in device 98 is formed by the cylinder insert 30 itself. Located within this second conical feed-in device 98 is the sealing element 32 in the parking position illustrated in FIGS. 6 and 7. The sealing element 32 is provided with a radial distance to the cylinder insert 30. The radial gap resulting therefrom allows the passage of fluid and/or gas for sterilization or disinfection of the embodiment after assembly of all the components. This parking position is defined by a locking element which presently is formed by an engaging pawl 100 integrally formed onto the casing base 2. This engaging pawl 100 can be seen in particular in FIGS. 10 to 12. The engaging pawl 100 is formed by cutting free the end of the guide sleeve 76 on the drive side. The engaging pawl 100 has a locking projection 102 which is illustrated in FIGS. 9 and 10 and in the parking position engages in a locking groove 104 being formed between two ring-shaped projections 106, 108 which are integrally formed on the plunger body 4 as a single part (cf. FIG. 10). The front ring-shaped projection 108 forms an almost strictly radially extending flank of the locking groove 104, whereas the rear ring-shaped projection 106 comprises an inclined flank which facilitates the advancement of the plunger body 4 from the parking position to a pumping or operating position. In a pumping or operating position, the sealing element 32 is in sealing abutment against the inner circumferential surface of the cylinder, presently the cylinder element 30. It can be assumed that FIGS. 9 and 10 represent the uppermost pumping position and FIG. 8 the lowest pumping position. The stroke of the plunger body 4 takes place between these two positions according to FIGS. 8 and 9.

The previously described parking position is locked by the configuration of the engaging pawl 100 and the locking groove 104. Axial pressure against the plunger body 4 from the drive side beyond a critical magnitude of the pressure force leads to the parking position being released and the plunger body 4 being displaced deeper into the casing and to the pumping position. In this pumping position, the projections 106, 108 guide the plunger body 4 also relative to the guide sleeve 76 which is formed by the casing base 2 (cf. FIGS. 9, 10), as a result of which higher running smoothness of the plunger body 4 during the pumping operation is obtained. The plunger body 4 is in particular prevented from buckling when axially loaded, so that the plunger body 4 can be produced from a relatively soft material, such as, for example, plastic material.

As illustrated in FIG. 6, the plunger body 4 in the parking position projects with its hammer head 68 over the casing base 2, whereby an optical indicator for verifying the parking position is provided. After joining to the drive, when the plunger bodies 4 are necessarily transferred from the parking position to a pumping position, the ends on the drive side with the hammer head 68 are each exposed within the casing base 2 and the axially open rear recess formed there in the drive region 20.

As the description of the embodiment illustrates, the inlet and outlet passages 44, 64 are in the pump module according to the invention formed between the cylinder insert 30 and the sealing element 32. They extend within a phase boundary between the valve block 26 and the cover element 28. The inlet passage 44 provided there distributes fluid introduced from an upper end near the inlet port 18 to the respective inlet valves 41. The fluid is guided in the phase boundary up to the inlet valves 41 at the outer edge of the phase boundary and accordingly at least partially surrounds the outlet passage 64. This outlet passage 64 communicates with several outlet valves 37, two in the present case. Within the phase boundary between the cover element 28 and the valve block 26, the outlet passage 64 directs the pressurized fluid up to a collection point which is flush with the discharge passage formed by the outlet port bushing 66. The collection point is there also located within the phase boundary between the cover element 28 and the valve block 26. The largest part of the inlet passage 44 and/or the outlet passage 64 is in particular formed within the phase boundary between the valve block 26 and the cover element 28. The largest part there represents at least 50%, preferably 60%, of the total length of the flow path of the respective passage within the pump module. This flow path for the inlet side begins with the inlet opening of the inlet port 18 and ends at the inlet valve 41. The respective path on the outlet side begins with the opening formed by the outlet port bushing 66 and ends at the outlet valve 37, presently the receiving space 94 of the corresponding valve 37.

Another important aspect of the invention is the pump unit 10 which consists of the valve block 26 and the cover element 28 with the valves 37, 41 and the cylinder inserts 30 installed therein. This pump unit 10 is preassembled. The invention can there also be varied in that the cylinder is formed by the casing base 2 itself or a cylinder element which is received in the casing base 2 and which is sealingly abutted against the valve block 26. It is there conceivable that the collar, which is apparent from FIG. 7, following the first conical feed-in device 96 abuts directly against a cylinder insert and—subject to pre-loading the casing base 2—presses the latter against the valve block 26, and in particular together with an O-ring which can be arranged at the phase boundary between the casing base 2 and the valve block 26 and thereby seals the cylinder insert thus provided.

Furthermore, it is significant that a parking position is defined in which the pump piston formed by the plunger body 4 is fixated such that the plunger body 4 is with a certain axial pressure displaced from the parking position to a pumping position. The sealing element 32 is in the parking position certainly not in abutment against the inner circumferential surface of the associated pump cylinder. The sealing element 32 is regularly provided with a radial distance from adjacent casing parts of the pump module so that the sterilization or disinfection can occur past the cylinder and the piston. All the flow-conducting parts of the pump module are there completely coated with the disinfecting or sterilizing agent and thereby effectively sterilized.

Figure 19:
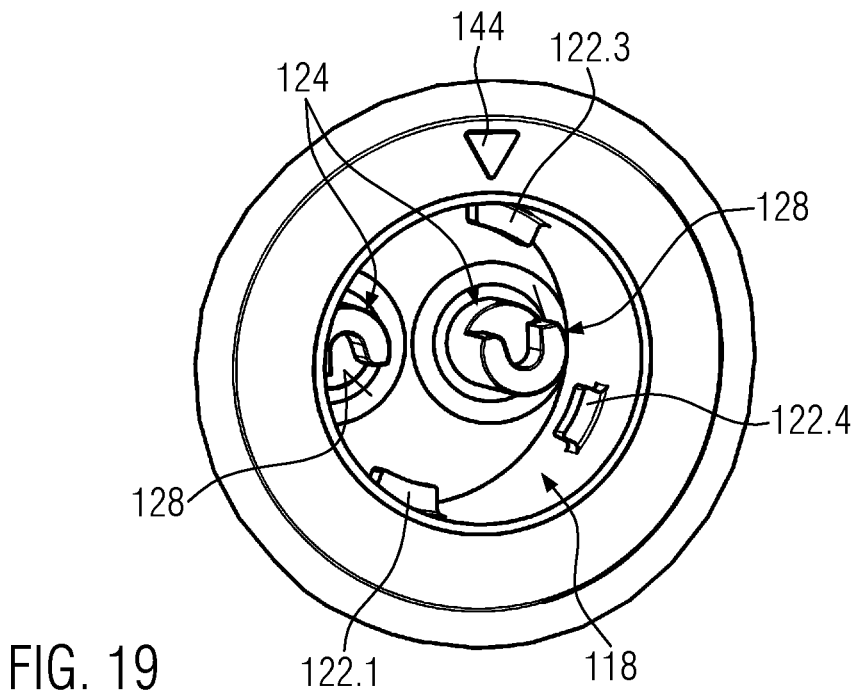
FIG. 19 shows the detail of FIG. 18 in an enlarged view without the pump module.
Figure 20:
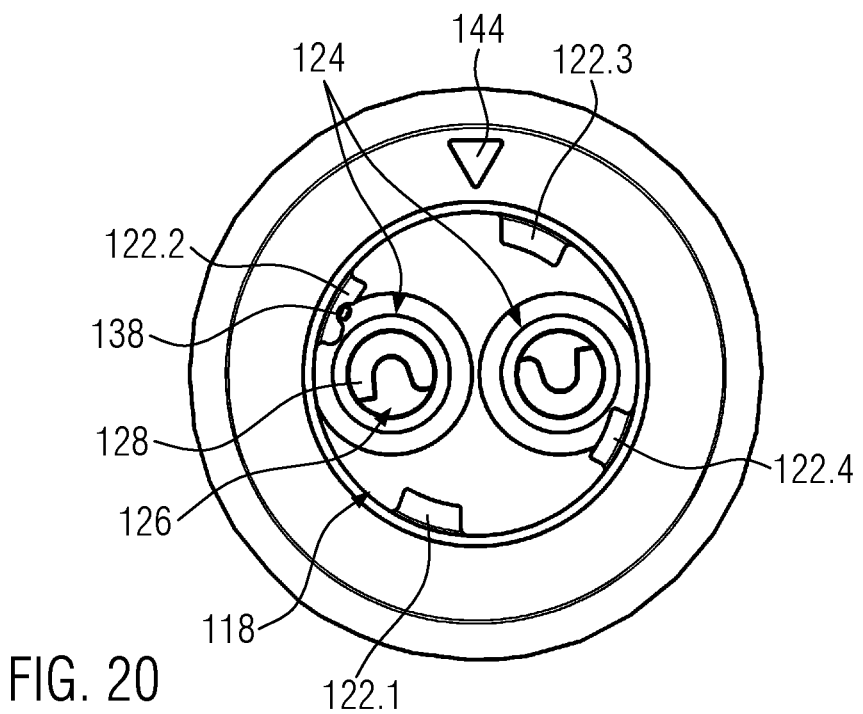
FIG. 20 shows the detail of FIG. 18 in a top view.

FIG. 19 shows a perspective side view of an embodiment of a drive unit 110 with a drive—being an electric drive—provided in a drive casing 112. A holder 114 protrudes from the drive casing 112 for holding a fluid bag. Exposed on the drive casing 112 are also various control elements 116 which serve to actuate the drive and to switch the drive on and off. Reference numeral 118 denotes a substantially cylindrical recess into which a pump module according to FIGS. 1 to 17 being denoted with reference numeral 120 is inserted and which is in comparison with these figures shown in simplified form. The casing base 2 comprises lugs 122 that protrude inwardly into the recess 118 and are embodiments of positive-locking elements of the present invention. Four lugs 122 are presently provided distributed on the circumference. The lug identified by reference numeral 122.4 has a smaller radial extension and a smaller extension in the circumferential direction than the other lugs 122.1 to 122.3 in order to allow for unique association of the pump module 120. Other types of a poka-yoke configuration are conceivable. Grooves with different angular offset relative to one another can be provided on the outer circumferential surface of the casing, in particular the casing base 2, so that the pump module 120 can be inserted into the recess 118 only in a predetermined manner. Exposed in the recess 118 are furthermore drive elements in the form of drive pushers 124 which are connected to the drive provided within drive casing 112 and which are drivable in reciprocating manner in the longitudinal direction. The drive pushers 124 form an abutment surface 126. Two drive pushers 124 are presently provided. A claw 128 being C-shaped in a top view projects over the abutment surface 126 and forms a hammer head seat 130 between itself and the abutment surface 126.

Figure 11:
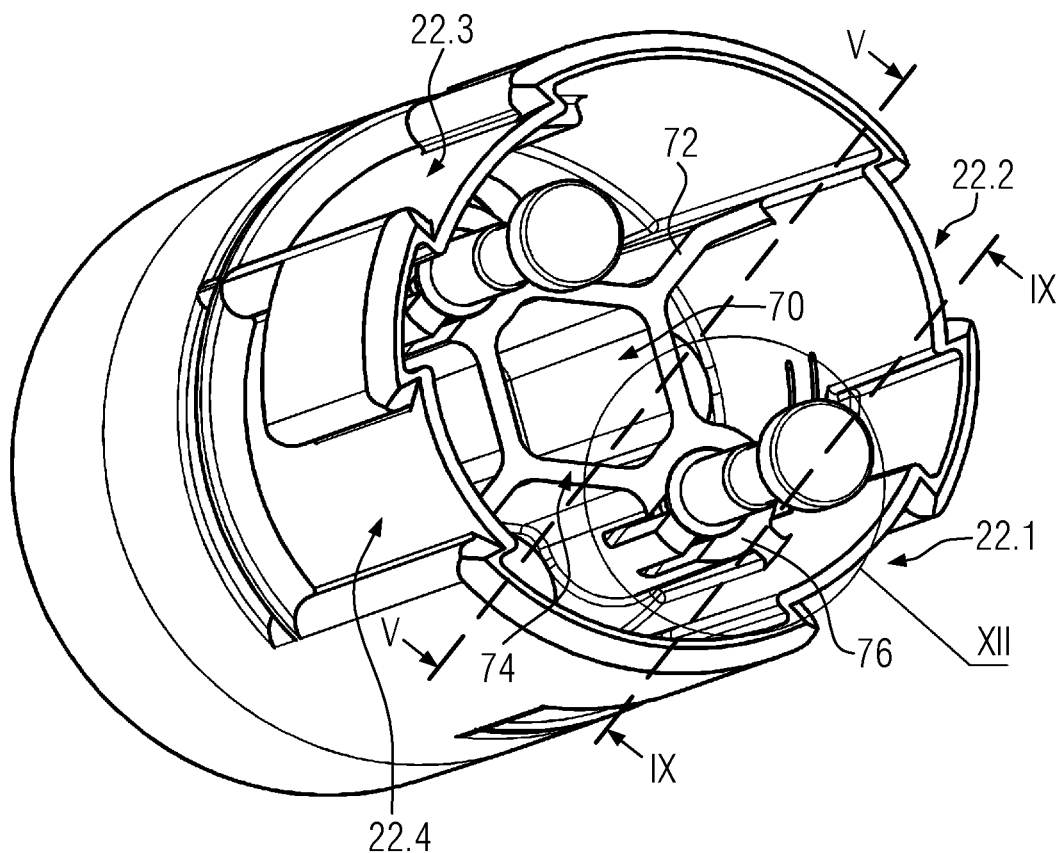
FIG. 11 shows a perspective rear view similar to FIG. 4.
Figure 12:
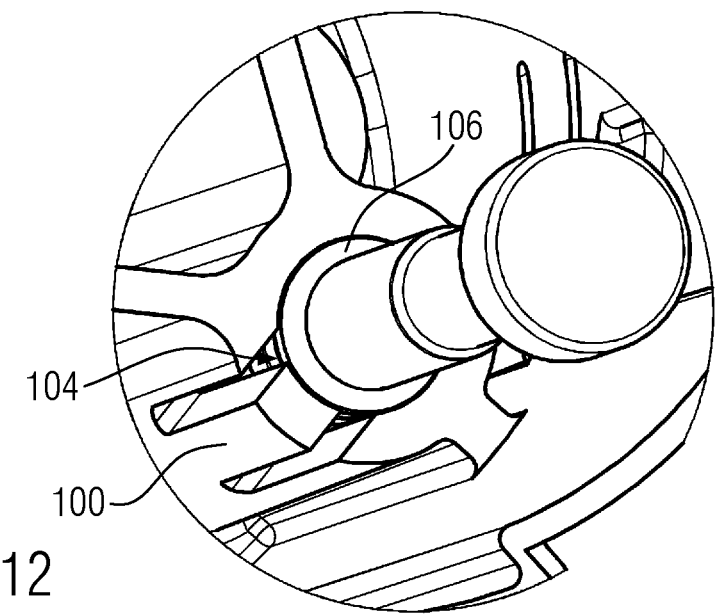
FIG. 12 shows enlarged detail XII according to FIG. 11.
Figure 16:
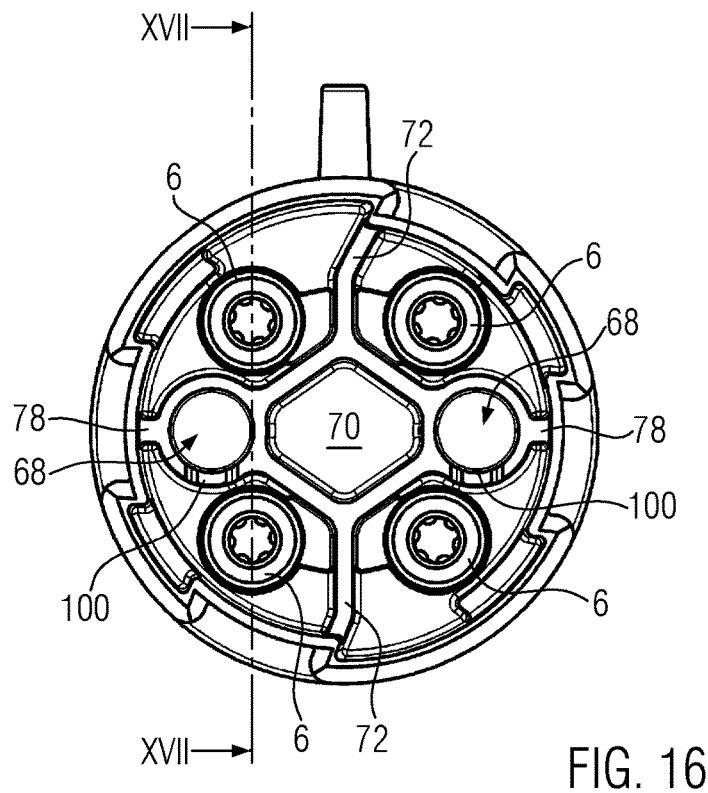
FIG. 16 shows a rear top view onto the embodiment.

As is evident in particular from FIGS. 11 and 16, of the four grooves 22 on the outer circumference of the casing base 2 extending strictly in the axial direction along the center longitudinal axis L, the groove designated with reference numeral 22.4 is formed adapted for the exact reception of the smaller lug 122.4. Due to the interaction of in particular the smaller lug 122.4 with the smaller groove 22.4, biunique orientation of the pump casing 120 is defined when joining, i.e. when inserting the pump module 120 into the recess 116. The pump module 120 can be inserted only at an angle perpendicular to a final position offset by 30° shown in FIG. 21c. This pivoted position is illustrated in FIG. 21b. The hammer head 68 projects beyond an end-side pump piston section 132 of each pump piston 4 that has a smaller diameter than the remaining pump piston 4. The hammer head 68 defines the face-side, connection-side end of the pump piston 4 and there forms a counter-surface 134 to the abutment surface 126.

The groove 22 together with the transverse groove 24 forms a guide for a bayonet lock with the respective lug 122 to first perform an axial insertion motion which then comes to an end when the lugs 122 abut against the inside lower end of the grooves 22, to thereafter be pivoted in a pivotal motion into the transverse groove 24 and thereby be axially locked. In the final position on the end side abutting against the transverse groove 24, a catch projection can be active which forms an anti-rotation lock between the pump module 112 and the drive casing 2 so that the pump module 112 is locked in its final position.

Figure 3:
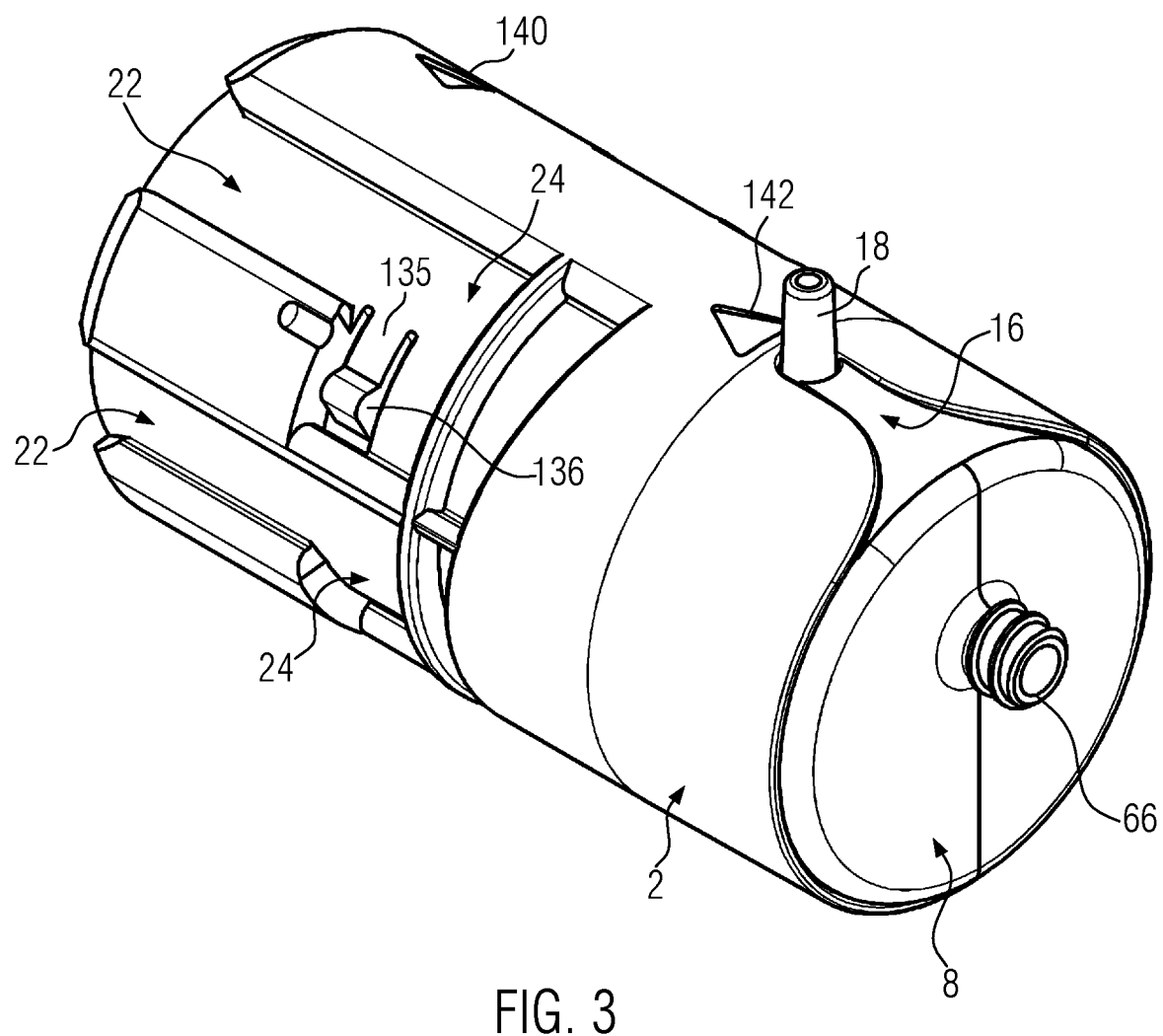
FIG. 3 shows a perspective side view according to the exploded view of FIG. 1 of the assembled pump module onto the front discharge region.
Figure 22A:
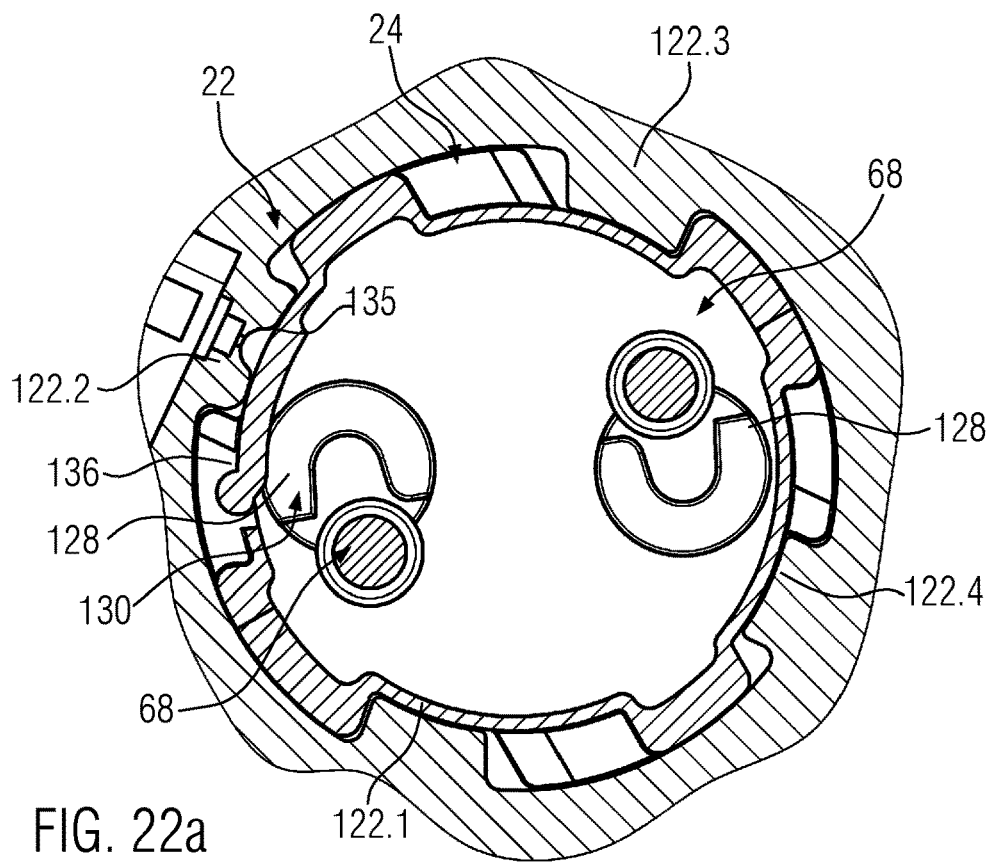

Drawn in FIG. 22a within the transverse groove 24 is further a catch and switch projection 136 formed on a spring arm and exposed in the transverse groove 24 and formed fixedly on the pump base 2 (cf FIG. 3). This catch and switch projection 37 is associated with a switch 138 provided centrically in the lug 122.2. The switch 138 is preloaded in the radial direction inwardly relative to the recess 118 and interacts accordingly with the catch and switch projection 136. The actuation of this switch 138 by means of the catch and switch projection 136 only gives rise to the possibility of driving the drive pusher 124. If the pump module 10 is accordingly not connected in the prescribed manner to the drive unit 1, then the drive unit can not be operated. The drive casing 112 is additionally provided with a reading unit which recognizes the correct orientation of the RFID ring 12 and thereby of the pump module 120 relative to the drive casing 112 and only then releases the output. This prevents operation of the device with the switch 138 being bridged.

Figure 21C:
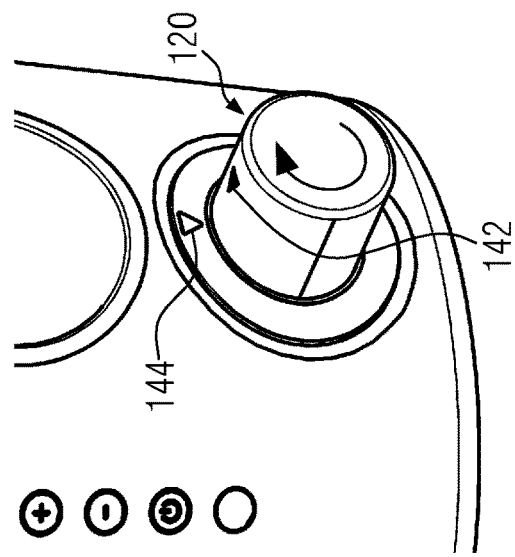
FIGS. 21a-c show a view similar to FIG. 19 with a sequence of steps for joining the pump module and FIG. 22a-c shows partially sectional top views of the interacting ends of the drive element and the drive counter-element and their relative position when pivoting during the joining process.
Figure 21B:
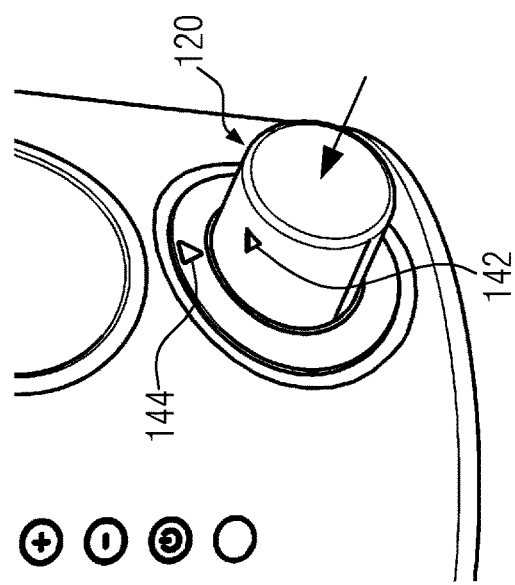
Figure 21A:
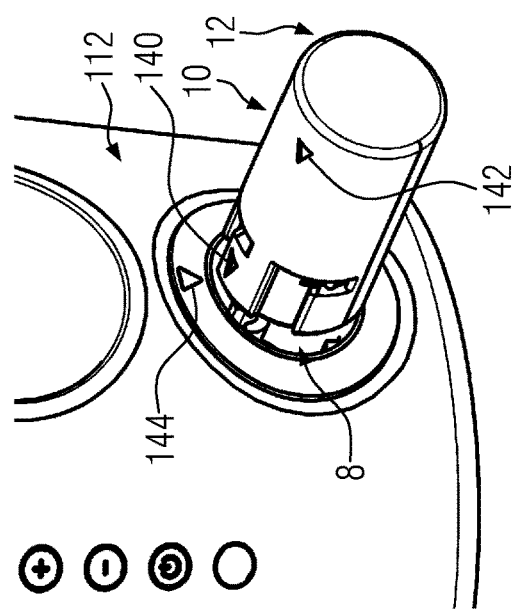

FIGS. 21a to c illustrate the insertion of the pump module 120 into the recess 118. As already mentioned above, pump module 120 is first pivoted by 30° in the counterclockwise direction relative to the final position to make the lugs 122 coincide with the grooves 22 (cf. FIG. 21a). The pivoted position is characterized by an alignment arrow 140 which can be clearly seen in FIG. 3 and is in FIG. 21a aligned with a position indicator 144 provided on the casing side. In this relative orientation, the pump module 120 can now be inserted into the recess 118. This axial insertion motion is guided by the lugs 122 which engage in the grooves 22 that are formed to correspond thereto. In the illustration according to FIG. 21b, this axial insertion, in FIG. 21b being illustrated by a straight-line arrow, is terminated. The pump module 120 is now inserted fully into the recess 118. Thereafter, the pump module 120 is pivoted by 30° in the clockwise direction, as indicated by the arrow in FIG. 21c. Following this pivotal motion by 30°, the pump module 120 has reached its final position. The final position is indicated to the user by a directional arrow 142 which is provided on the outer periphery of the casing base 2 and which is in the final position aligned with a position indicator 144 provided on the drive casing 2. The directional arrow 142 also indicates the direction of insertion for the pump module 2 into the recess 8.

When joining the pump module 120 and the drive casing 112, the drive pushers 124 and the pump pistons 4 are approximate to each other. Due to the axial guidance of the lugs 122 in the grooves 22, the counter-surface 134 formed by the hammer head 68 is at least in part located above the abutment surface 126 formed by the drive pusher 124 (cf. FIG. 22a). A progressive axial motion finally leads to the pump piston 4 being in abutment at the end side against the abutment surface 126. As the pump module 120 continues to approach the drive casing 112, the parking position is released and the pump piston 4 is forced deeper into the casing base 2 and to a pumping position. No further relative axial motion between the drive pusher 124 and the associated pump piston 4 is thereafter given.

The respective hammer head 68 of the two pump pistons 4 is there located in an eccentric position relative to the center of the drive pusher 124, which is shown in FIG. 22a. The casing base 2 is after the axial abutment of both pump pistons 4 against the drive pushers 124 typically displaced by a further minor distance axially relative to the drive casing 2, so that it is ensured that axial abutment of the pump piston 4 is always reliably obtained against the drive pusher 124 until the axial final position has been reached when joining the pump module 120 and drive casing 112, ahead of casing base 2 is pivoted relative to the drive casing 112. The configuration is certainly to be such that reliable abutment of the pump piston 4 against the drive pusher 124 is after completion of the axial insertion motion obtained in any conceivable position of drive pusher 124, even in a position where the drive pusher 124 is in the lowest position within the recess 8.

Figure 22B:
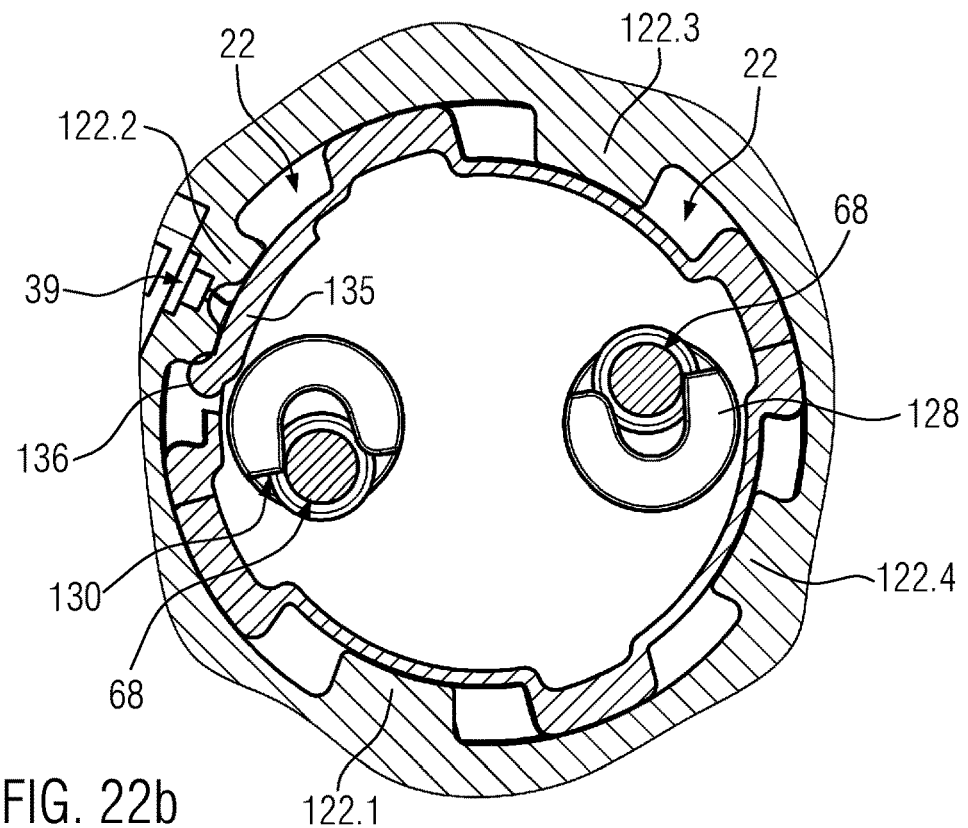
Figure 22C:
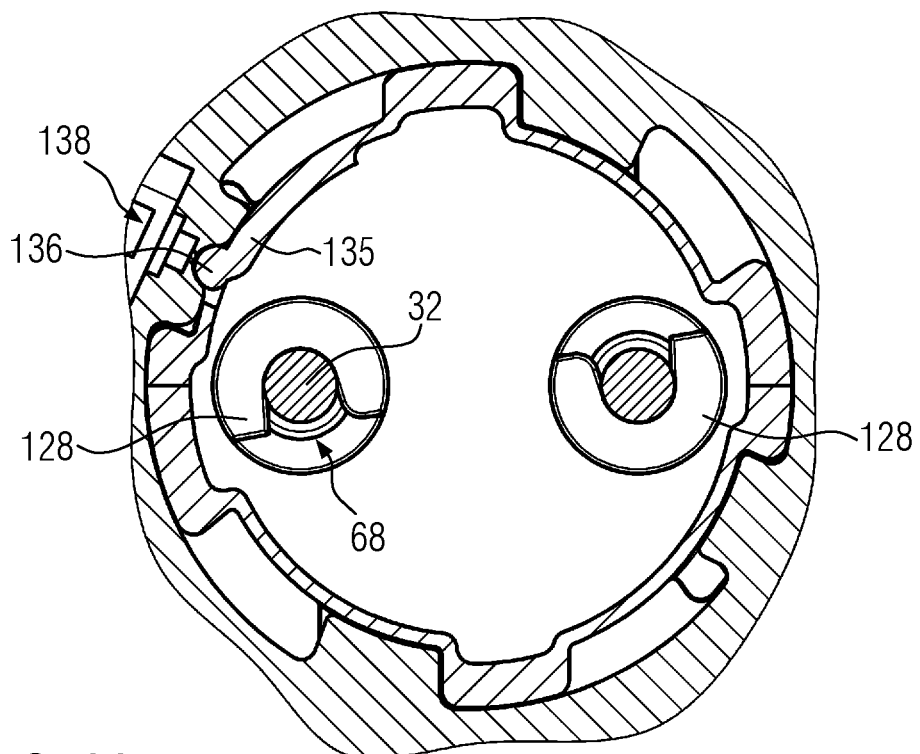

After this axial final position has been reached, the pump module 120 is then pivoted in the clockwise direction. The hammer heads 68 being disposed eccentric to the center of this pivotal motion are thereby—as illustrated in FIGS. 22a to 22c—with their counter-surface 134 in a sliding manner displaced on the abutment surface 126 relative to drive pusher 124, namely in a plane extending perpendicular to the direction of insertion. The previously eccentric arrangement of the pump pistons 4 relative to drive pushers 124 according to FIG. 22a thereafter, via an intermediate position shown in FIG. 22b, approaches the final position shown in FIG. 22c. In this final position, the lugs 122 abut against stops which are formed by the transverse grooves 24. The casing base 2 is commonly locked against the drive casing 2. The pump pistons 4 are arranged substantially concentric to the drive pushers 124. Each claw 128 engages over the associated hammer head 68. The hammer head 68 is by engagement of the hammer head seat 130 comprising the claw 128 held in an axially positive-locking manner. The hammer head seat 130 is typically in the axial direction matched exactly to the height of the hammer head 68 so that a play-free axial positive-locking connection between drive pusher 124 and the pump piston 4 arises.

LIST OF REFERENCE NUMERALS 2 casing base
4 plunger body/pump piston
6 tensioning screw:
8 head element
10 pump unit
12 RFID ring
14 discharge region
16 axial slot
18 inlet port
20 drive region
22 groove
24 transverse groove
26 valve block
28 cover element
30 cylinder insert
32 sealing element
34 valve liner
36 valve ball
37 outlet valve
38 valve liner
40 valve ball
41 inlet valve
42 inlet valve bore
44 inlet passage
46 projection
50 outlet valve bore
52 fitting element
54 sealing surface
56 fitting bore
58 outlet bore
60 through bores
62 annular surface
64 outlet passage
66 outlet port bushing
68 hammer head
70 center recess
72 radial web
74 polygon structure
76 guide sleeve
78 further radial web
80 partition wall
82 passage bore
83 sealing ring
84 cylinder insert receiving bore
86 ring collar
88 support rib
90 sleeve segment
92 passage bore
94 receiving space
96 first tapered feed-in device
98 second tapered feed-in device
100 engaging pawl
102 locking projection
104 locking groove
106 ring-shaped projection
108 ring-shaped projection
110 drive unit
112 drive casing
114 holder
116 control element
118 recess
120 pump module
122 lugs
124 drive pusher
126 abutment surface
128 claw
130 hammer head seat
132 pump piston section
134 counter-surface
135 spring arm
136 catch and switch projection
138 switch
140 alignment arrow
142 directional arrow
144 position indicator
L center longitudinal axis

The invention claimed is:

1. A pump module comprising a casing in which at least one pump piston is mounted in a reciprocating manner and provided with at least one sealing element which in a pumping operation sealingly abuts against a cylinder, and further comprising a locking element which is arranged on said casing and which in a parking position, in which said sealing element does not abut against said cylinder, interacts with a locking counter-element provided on said pump piston for fixing said pump piston in the parking position; wherein said locking element comprises a pawl formed integrally on the casing and elastically preloaded radially against the pump piston, and said locking counter-element comprises two radial projections provided at an axial distance from one another between which said locking element engages in the parking position.

2. The pump module according to one claim 1, wherein said locking counter-element is in the pumping operation guided in a guide cylinder of said casing being axially disposed ahead of said cylinder.

3. The pump module according to claim 1, further comprising a conical in-feed device disposed ahead of said cylinder, wherein the smallest inner diameter of said conical in-feed device substantially corresponds to the inner diameter of said cylinder.

4. The pump module according to claim 1, wherein said pump piston comprises a plunger body formed from plastic material and at one end comprising a positive-fit element for coupling said piston to a drive associated with said piston and at its other end being formed adapted for fastening said sealing element.

5. The pump module according to claim 4, wherein in the parking position said casing projects over said one end.

6. The pump module according to claim 1, wherein in the parking position said casing is covered by a cover cap placed on said casing.

7. The pump module according to claim 1, further comprising a cylinder insert which is associated with said pump piston and which in pumping operation encloses said sealing element between itself and a plunger body.

8. The pump module according to claim 7, wherein said cylinder insert at a face side abuts against a valve block which forms inlet and outlet passages to said cylinder insert and receives inlet and outlet valve elements.

9. A pump module comprising a casing in which at least one pump piston is mounted in a reciprocating manner and provided with at least one sealing element which in a pumping operation sealingly abuts against a cylinder, and further comprising a locking element which is arranged on said casing and which in a parking position, in which said sealing element does not abut against said cylinder, interacts with a locking counter-element provided on said pump piston for fixing said pump piston in the parking position; further comprising a conical in-feed device disposed ahead of said cylinder, wherein the smallest inner diameter of said conical in-feed device substantially corresponds to the inner diameter of said cylinder; and wherein in the parking position said sealing element is arranged in said conical in-feed device such that a radial gap is set between said sealing element and a casing wall circumferentially surrounding said sealing element to allow for at least one of a fluid and a gas to flow around the pump piston for sterilization or disinfection.

10. The pump module according to claim 9, wherein said radial gap is at least $1/10$ mm.

11. A pump module comprising a casing in which at least one pump piston is mounted in a reciprocating manner and comprises a plunger body provided with at least one sealing element which in a pumping operation sealingly abuts against a cylinder and further comprising a cylinder insert which is associated with said pump piston and which in pumping operation encloses said sealing element between itself and said plunger body and wherein an end face of said cylinder insert abuts against a valve block which forms inlet and outlet passages to said cylinder insert and receives inlet and outlet valve elements.

12. The pump module according to claim 11, wherein said inlet valve and said outlet valve each comprise a valve liner, wherein the valve liner of said inlet valve abuts against the cylinder insert.

13. The pump module according to claim 11, wherein said inlet valve and said outlet valve each comprise a valve liner, wherein the valve liner of said outlet valve abuts against a cover element which is attached to said valve block to enclose an inlet passage communicating with said inlet valve and an outlet passage communicating with said outlet.

14. The pump module according to claim 13, wherein said cover element is formed from laser-transparent material, wherein said valve block is formed from plastic material absorbing laser beam plastic and wherein said cover element is laser beam welded against said valve block to enclose said inlet passage communicating with said inlet valve and said outlet passage communicating with said outlet passage.

* * * * *